(12) United States Patent
Fujita et al.

(10) Patent No.: US 8,393,226 B2
(45) Date of Patent: Mar. 12, 2013

(54) INCLUSION RATING METHOD

(75) Inventors: Shinji Fujita, Fujisawa (JP); Yukitaka Murakami, Fukuoka (JP)

(73) Assignees: NSK Ltd., Tokyo (JP); Kyushu University, National University Corporation, Fukuoka (JP)

( * ) Notice: Subject to any disclaimer, the term of this patent is extended or adjusted under 35 U.S.C. 154(b) by 150 days.

(21) Appl. No.: 12/846,409

(22) Filed: Jul. 29, 2010

(65) Prior Publication Data
US 2012/0024077 A1 Feb. 2, 2012

(51) Int. Cl.
*G01N 3/08* (2006.01)
(52) U.S. Cl. ............................................ 73/826; 73/834
(58) Field of Classification Search .................... 73/826, 73/830, 834
See application file for complete search history.

(56) References Cited

U.S. PATENT DOCUMENTS

| | | | |
|---|---|---|---|
| 4,520,052 A * | 5/1985 | Skowronek et al. ......... | 427/99.5 |
| 6,546,808 B2 * | 4/2003 | Sawai et al. .................... | 73/808 |
| 6,912,913 B2 * | 7/2005 | Murakami ...................... | 73/808 |

FOREIGN PATENT DOCUMENTS

| | | |
|---|---|---|
| JP | 9-125200 A | 5/1994 |
| JP | 6-192790 A | 7/1994 |
| JP | 8-240586 A | 9/1996 |
| JP | 9-125199 A | 5/1997 |
| JP | 11-230961 A | 8/1999 |
| JP | 3-944568 B2 | 7/2007 |
| JP | 2008-280612 A | 11/2008 |

OTHER PUBLICATIONS

Jaques Monnot, et al.; "Relationship of Melting Practice, Inclusion Type, and Size with Fatigue Resistance of Bearing Steels"; ASTM STP, 987, 1988; p. 149-165.
Akira Adachi, et al.; "Rotating Bending Fatigue Phenomenon of JIS SUJ2 Bearing Steel"; Denki Seiko (Electric Furnace Steel); 1975; vol. 46, No. 3, pp. 176-182.
Yukitaka Murakami; "Metal Fatigue, Micro-Defects and Effect of Inclusions", Yokendo, 1993; pp. 94-99; ISBN4-8425-9302-4 C3053.
Shoichi Fukui; "The Effect of Tempering on the Delayed Fracture Characteristics of Low-Alloy Steels"; The Iron and Steel Institute of Japan; 1969, vol. 55 No. 12, pp. 151-161.
Shirong Zhuo, et al.; "Statistics of Extremes Analysis of Nonmetallic Inclusions Based on 3D Inspection"; The Iron and Steel Institute of Japan, vol. 87, No. 12; 2001; pp. 748-755.
Rinya Takahashi, et al.; "Prediction of the Maximum Size in Wicksell's Corpuscle Problem"; Annals of the Institute of Statistical Mathematics; 1998; vol. 50 No. 2; pp. 361-377.
Rinya Takahashi, et al.; "The Maximum Size of the Planar Sections of Random Spheres and its Application of Metallurgy"; Annals of the Institute of Statistical Mathematics; 1996; vol. 48 No. 1, pp. 127-144.

(Continued)

*Primary Examiner* — Max Noori
(74) *Attorney, Agent, or Firm* — Sughrue Mion, PLLC

(57) ABSTRACT

An inclusion rating method includes carrying out a tensile test on a test specimen, which is made of a metallic material and charged with a hydrogen, to cause a fracture originating from a nonmetallic inclusion affected by the hydrogen in the test specimen, identifying a type of the nonmetallic inclusion, measuring a size of the nonmetallic inclusion, and evaluating a cleanliness of the metallic material by obtaining a distribution function of the size of the nonmetallic inclusion.

15 Claims, 10 Drawing Sheets

OTHER PUBLICATIONS

Keizo Onishi, et al.; "Room Temperature Hydrogen Gas Embrittlement of Structural Steel"; The Iron and Steel Institute of Japan; 1983; vol. 69 No. 2; pp. A136-A139.

Tatsu Fujita, et al.; "Physical Metallurgy and SCC in High Strength Steels"; NZCE-5; 1997, pp. 736-746.

Shinji Fujita, et al.; "A New Inclusion Rating Method by the Tensile Test with Hydrogen-precharged Specimens"; The Iron and Steel Institute of Japan, Dec. 2009; vol. 95 No. 12; pp. 870-879.

Shinji Fujita; "Effect of Hydrogen on fatigue properties of bearing steel—Shear mode fatigue behavior and a new inclusion rating method"; Public Presentation at Kyushu University, Jul. 31, 2009; 1-60.

Communication dated Dec. 4, 2012, issued by the Japanese Patent Office in Japanese Application No. 2009-065789.

Nishiguchi et al., "Effects of Hydrogen and Pre-strain on Tensile Properties of Carbon Steel STPG 370 (0.19 C-0.21 Si-0.56 Mn, mass%) for 1 MPa Hydrogen Pipelines," *Transactions of the Japan Society of Mechanical Engineers Series A*, vol. 74, No. 743, pp. 1016-1025 (Jul. 25, 2008).

\* cited by examiner

INCLUSION RATING METHOD

FIELD OF INVENTION

The present invention concerns a method of evaluating inclusions contained in a metallic material.

DESCRIPTION OF RELATED ART

It is said that about 80% of fracture accidents in machineries, structures, etc. is attributable to fatigue fracture and it is extremely important to prevent the fracture accidents caused by the fatigue fracture. For high strength steels having a hardness of HV400 or more, since it has been known that defects or nonmetallic inclusions contained in materials are origins of the fatigue fracture, it is extremely important to investigate nonmetallic inclusions contained in the materials.

Various nonmetallic inclusion rating methods have been proposed, e.g., the ASTM method in the United States, the VDEh method in Germany, and the JIS lattice point counting method in Japan.

However, it is pointed out that there is no distinct correlation between the inclusion rating index number and the fatigue strength defined by these rating methods (see, e.g., J. Monnot, B. Heritier, J. Y. Cogne, "Relationship of Melting Practice, Inclusion Type, and Size with Fatigue Resistance of Bearing Steels", ASTM STP, 987, 1988, p. 149, and Akira Adachi, Hideo Shoji, Ayao Kuwabara, Yoshiyuki Inoue, "Rotating Bending Fatigue Phenomenon of JIS SUJ2 Bearing Steel", Denki Seiko (Electric Furnace Steel) Vol. 46, No. 3, 1975, pp. 176-182). This is because the related art nonmetallic inclusion rating methods are not proposed based on the result of detailed observation on fatigue phenomena. What is deleterious to the fatigue strength is the largest nonmetallic inclusion contained in the material whereas the chemical composition and the distribution density of the nonmetallic inclusions essentially has less correlation.

A method of estimating the size of the largest nonmetallic inclusion contained in a material includes an inclusion rating method by an extreme value statistical method (see, e.g., JP 11-230961 A). The extreme value statistical method is a method of estimating the size of the largest nonmetallic inclusion among the entire nonmetallic inclusions contained in a material based on the distribution of nonmetallic inclusions in a portion of the material.

Further, a method of quantitatively evaluating the cleanliness of metallic materials includes a method of evaluation by extracting nonmetallic inclusions from a metallic material by acid dissolution (see, e.g., JP 9-125199 A and JP 9-125200 A), and a method of melting a metallic material by an electron beam melting method (EB melting method) and observing floating nonmetallic inclusions by a microscope (see, e.g., JP 6-192790 A).

On the other hand, it is considered that when a fatigue test is carried out, fracture is caused from the largest nonmetallic inclusion among nonmetallic inclusions contained in a control volume (see, e.g., Yukitaka Murakami, "Metal Fatigue, Micro-Defects and Effect of Inclusions", Yokendo, 1993, p. 94). In view of this, there a method of actually carrying out a fatigue test to cause fracture originating from nonmetallic inclusions in a metallic test specimen, measuring the size of the nonmetallic inclusions, and estimating the size of the largest nonmetallic inclusion among the nonmetallic inclusions in a control volume by an extreme value statistical method (see, e.g., JP 3944568 B).

By the way, it has been known long since that hydrogen deteriorates the strength of metallic materials and the phenomenon is referred to as "hydrogen embrittlement," "hydrogen-assisted cracking", or "delayed fracture" and various studies have been made so far. However, at present, mechanisms that hydrogen deteriorates the strength of metallic materials have not yet been analyzed completely.

Fukui et al. determined the ratio of a bending strength to a static bending strength not causing delayed fracture in an aqueous solution of hydrogen chloride for 30 hours or more (hereinafter referred to as delayed fracture strength ratio) by using low alloy steels formed at various tempering temperature and showed that the delayed fracture strength ratio lowered remarkably at a hardness of HRC40 (HV375) or more (see, e.g., Shoichi Fukui, "The Effect of Tempering on the Delayed Fracture Characteristics of Low Alloy-Steels", Tetsu-to-Hagane, The Iron and Steel Institute of Japan, Vol. 55, No. 12, 1969, pp. 151-161).

The nonmetallic inclusion rating using the extreme value statistical method is capable of quantitatively estimating the size of the largest nonmetallic inclusion $\sqrt{area}_{max}$ where, $\sqrt{area}_{max}$ is defined as a square root of the area of a largest inclusion projected onto a plane perpendicular to the maximum principal stress, based on microscopic observation and thus is utilized by many researchers.

However, it is pointed out that error sometimes increases when the size of the largest nonmetallic inclusion as an origin of fatigue fracture in a relatively small reference area $S_0$ is estimated by microscopic observation in a case of using SCM 435 as a metallic material (see, e.g., Shirong Zhou, Yukitaka Murakami, Yoshihiro Fukushima, Stefano Beretta, "Statistics of Extremes Analysis of Nonmetallic Inclusions Based on 3D inspection", Tetsu-to-Hagane, The Iron and Steel Institute of Japan, Vol. 87, No. 12, 2001, pp. 748-755). This is because the type (component) is different between the nonmetallic inclusions as origins of the fatigue fracture and the nonmetallic inclusions observed by the microscope.

Further, for accurately evaluating nonmetallic inclusions of a type as origins for the fatigue fracture by microscopic observation, it has been pointed out that the critical value $S_{crit}$ of the inspection area is about 10,000 mm$^2$ or more in SCM 435. Accordingly, it is considered that finding of a large nonmetallic inclusion as an origin for the fatigue fracture by microscopic observation is not always easy and is expensive.

With regard to the method of extracting nonmetallic inclusions from metallic materials by acid dissolution, in a case where a number of nonmetallic inclusions are chained in the form of a cluster, the largest nonmetallic inclusion in a control volume may not be measured accurately. Further, since there is also a possibility that nonmetallic inclusions are dissolved in the acid, they cannot be considered as a best method for evaluating various no-metal inclusions.

With regard to the method of melting a metallic material by an electron beam, in a case where a plurality of nonmetallic inclusions are chained in the form of a cluster, the largest nonmetallic inclusion in a control volume may not be measured accurately.

Further, with regard to the method of evaluating nonmetallic inclusions by utilizing a fatigue test, quick evaluation is possible since the test is completed in about 10 minutes at the number of stress cycles of about $10^7$ times and in about 100 minutes at the number of stress cycles of about $10^8$ times at a frequency of 20 kHz when they are evaluated by using an ultrasonic fatigue testing machine. However, the ultrasonic fatigue testing machine involves a problem that an hourglass type test specimen has to be used. The control volume of a specimen in a case of using, for example, the ultrasonic fatigue testing machine described in JP 3944568 B is as small as 33 mm$^3$. The control volume is 1272 mm$^3$ in a case of a fatigue test specimen used in a hydraulic servo-assisted fatigue testing machine to be described later. Since data obtained from a test specimen of a large control volume has a high reliability, a further improvement is demanded for the inspection of nonmetallic inclusions by using the ultrasonic fatigue testing machine.

In the hydraulic servo-assisted fatigue testing machine, since a specimen having a parallel portion can be used, it is possible to use a test specimen having a control volume 10 times as large as the ultrasonic fatigue testing machine. However, the cycle frequency of the hydraulic servo-assisted fatigue testing machine is lower compared with that of the ultrasonic fatigue testing machine and it is about 20 to 1,000 Hz. In a case where the cycle frequency is 20 Hz, it requires about 6 days at the number of stress cycles of about $10^7$ times and requires as much as about 58 days at the number of stress cycles of about $10^8$ times. Even at the cycle frequency of 500 Hz, it requires about 6 hours at the number of stress cycles of about $10^7$ cycles and as much as about two days at the number of stress cycles of about $10^8$ times. Further, in an axial load fatigue testing machine, since a bending stress tends to exert on a test specimen, it involves a problem that attachment of the test specimen is troublesome.

BRIEF SUMMARY

Illustrative aspects of the present invention address one or more of the problems described above, and provide a convenient and speedy inclusion rating method.

The inventors have found that, when a tensile test is carried out with a hydrogen-charged test specimen, occurrence of fracture originating from the largest nonmetallic inclusion in a control volume of the test specimen is facilitated due to the effect of hydrogen, so that the test specimen is fractured with a low load. As a result, it has been found that nonmetallic inclusion rating can be carried out stably in a short time and at low cost. It has further been found that, by analyzing the size of the nonmetallic inclusions from which the fracture is originated using an extreme value statistical method, the size of the largest nonmetallic inclusion in the metallic material can be estimated.

That is, according to an illustrative aspect of the present invention, an inclusion rating method includes carrying out a tensile test on a test specimen, which is made of a metallic material and charged with a hydrogen, to cause a fracture originating from a nonmetallic inclusion affected by the hydrogen in the test specimen, identifying a type of the nonmetallic inclusion, measuring a size of the nonmetallic inclusion, determining a distribution function of the size of the nonmetallic inclusion, and evaluating a cleanliness of the metallic material based on the distribution function. The cleanliness of the metallic material may be evaluated in a similar manner as described above by carrying out the tensile test while charging the hydrogen to the metallic test specimen.

Other aspects and advantages of the invention will be apparent from the following description, the drawings and the claims.

DETAILED DESCRIPTION

Figure 1:
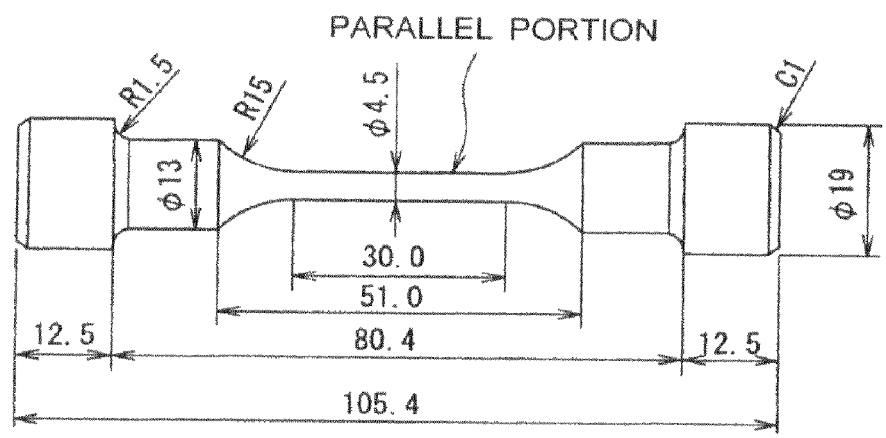
FIG. 1 is a diagram illustrating a shape and dimensions of a tensile test specimen.

Hereinafter, exemplary embodiments of the present invention will be described in detail with reference to the drawings.

According an exemplary embodiment, first, a tensile test specimen made of a metallic material is prepared. While the type of the metallic material is not particularly restricted, bearing steels (for example, high carbon chromium bearing steel SUJ2), structural steels (for example, SCM 435), spring steels (for example, SUP 12), tool steels, stainless steels, etc., according to JIS can be used.

Then, a tensile test specimen is charged with hydrogen. The method of hydrogen charge is not particularly restricted and includes, for example, a method of immersing a tensile test specimen in an aqueous acidic solution (for example, aqueous solution of ammonium thiocyanate), a method of exposing a tensile test specimen to a hydrogen gas, a method of applying an electric current to a tensile test specimen while immersing the specimen in an electrolyte (for example, an aqueous solution of sodium chloride and ammonium thiocyanate or an aqueous solution of sulfuric acid and arsenous acid), etc. Hydrogen may be charged to a tensile test specimen, or hydrogen may be charged to a metallic material before fabrication into the shape of a tensile test specimen and a tensile test specimen may be fabricated from hydrogen charged metallic material.

Then, a tensile test (static test) is carried out to the hydrogen charged tensile test specimen to fracture the tensile test specimen. Since the hydrogen charged tensile test specimen easily fractured from the largest nonmetallic inclusion a in the control volume of the tensile test specimen under the effect of hydrogen, it is fractured at a lower load compared with that not undergoing the hydrogen charge. In this case, it is preferable that hydrogen exists uniformly in the control volume of the tensile test specimen.

The hydrogen charge may be carried out before or during the tensile test. That is, the tensile test specimen may be charged with hydrogen during the tensile test. For example, a tensile test may be carried out while charging hydrogen to the tensile test specimen by immersing the tensile test specimen into an aqueous acidic solution (e.g., an aqueous solution of ammonium thiocyanate), by exposing the tensile test specimen to a hydrogen gas, or by immersing the tensile test specimen into an electrolyte (e.g., an aqueous solution of sodium chloride and ammonium thiocyanate or an aqueous solution of sulfuric acid and arsenous acid).

Then, nonmetallic inclusions in the fractured tensile test specimen are analyzed. That is, the type of nonmetallic inclusions as origins of fracture are identified, the size of the nonmetallic inclusions is measured and a distribution function of the size of the nonmetallic inclusion is determined. The cleanliness of the metallic material can be evaluated by the distribution function obtained as described above. According to the evaluation method described above, the nonmetallic inclusions can be evaluated in a short time and at low cost, as well as stable evaluation is possible. Further, nonmetallic inclusions as origins for fatigue fracture can be evaluated easily and accurately by using a usual tensile testing machine without using a special testing machine such as an ultrasonic fatigue testing machine. Accordingly, this method can be applied to the evaluation of quality assurance and quality improvement of metallic materials such as iron and steel materials. Particularly, this is suitable to the evaluation of rolling bearing steels and steels for precision products requiring high cleanliness.

The control volume is a volume of a portion of a test specimen undergoing a high stress that may cause an origin of fracture. As for test specimens that are usually used in a tensile test or a fatigue test (dynamic test), a volume of a parallel portion between the ends of the test specimen to which a stress is input corresponds to the control volume. In a case of a test specimen having a cylindrical parallel portion, the control volume Vs can be expressed as $0.25 \pi d^2 l$, in which d is a diameter of the parallel portion, and l is a length of the parallel portion.

Further, it is preferable to define the size of the nonmetallic inclusion from which the fracture is originated as a square root for the projected area of the nonmetallic inclusion. That is, cleanliness of a metallic material can be evaluated by measuring an area projected in the direction of a tensile axis in a tensile test with respect to the nonmetallic inclusion from which the fracture is originated, calculating the square root of the projected area $\sqrt{area}$, and based on the distribution function of the square root of the projected area $\sqrt{area}$. In this case, when the square root of the projected area $\sqrt{area}$ is analyzed by the extreme value statistical method, the size of the largest nonmetallic inclusion among the nonmetallic inclusions in the metallic material can be estimated.

The square root of the projected area $\sqrt{area}$ corresponds to an equivalent defect size. In a case of a fatigue test to be described later, a projected area as viewed from the direction of a main stress in the fatigue test is measured for the nonmetallic inclusion as the origin of fracture and this is defined as the projected area $\sqrt{area}$. Further, in a case of observing nonmetallic inclusions by metal microscopic observation to be described later, the area of a nonmetallic inclusion is measured based on an obtained microscopic image (for example, microscopic photograph) and this is defined as the projected area $\sqrt{area}$.

Further, the extreme value statistical method means a method of analyzing an extreme value distribution. The extreme value distribution means such a distribution that defines a maximum value and a minimum value in each of assembles when assemblies for a predetermined number of data are taken out from a group of data defined by a certain basic distribution function. Even when the basic distribution is a normal distribution or exponential distribution, the extreme value distribution thereof forms a distribution different from the basic distribution.

Hereinafter, examples of the present invention will be described in detail with comparative examples, and related art examples.

Nonmetallic Inclusion Rating Method by Metal Microscopic Observation

Description is to be made to a related art example of evaluating nonmetallic inclusions contained in a metallic material by metal microscopic observation. The evaluation method is a method described in JP 11-230961 A.

The type of the metallic material is high carbon chromium bearing steel SUJ2 (SAE52110) which is identical with that used in a related art example (fatigue test) and a working example (tensile test) to be described later. The alloy ingredients comprises, as the compositional ratio, 1.00 mass % of carbon, 1.44 mass % of chromium, 0.26 mass % of silicon, 0.36 mass % of manganese, 0.03 mass % of molybdenum, 0.011 mass % of phosphorus, 0.007 mass % of sulfur, 0.10 mass % of copper, 0.07 mass % of nickel, 0.002 mass % of titanium, 6 mass ppm of oxygen, and the balance of iron.

By using such a metallic material, a test specimen for metal microscopic observation was prepared as described below. A parallel portion of a tensile test specimen in FIG. 1 to be described later was cut such that a plane perpendicular to the longitudinal direction of a tensile test specimen (in the direction of the tensile axis) forms a fracture surface to cut out a cylindrical test specimen of 4.5 mm diameter and 2.0 mm thickness for metal microscopic observation. The tensile test specimen is a material not yet used for the tensile test.

A cylindrical test specimen for metal microscopic observation was buried in a resin and, after polishing only one of upper and lower surfaces of the test specimen for metal microscopic observation as an observation surface by using emery paper and surface polishing the same to #2000 (hereinafter, surface finishing using emery paper is referred to as emery polishing), buff polishing was carried out. The inspection area $S_0$ is the entire surface of the test specimen for metal microscopic observation, which is 15.9 mm² (4.5×4.5×π/4). Forty locations were observed by a metal microscope (number of inspection view fields: 40).

The metal microscopic photograph at the observed surface was subjected to image processing by an image processing apparatus and the size of the largest nonmetallic inclusion $\sqrt{area}_{max}$ (square root of projected area of the largest nonmetallic inclusion) among nonmetallic inclusions in the inspection area $S_0$ was measured. Then, the nonmetallic inclusions were identified by using an energy dispersion X-ray spectrometer (EDX) attached to a scanning electron microscope (SEM). An acceleration voltage was 20 kV in SEM observation and EDX spectroscopy.

Figure 2:
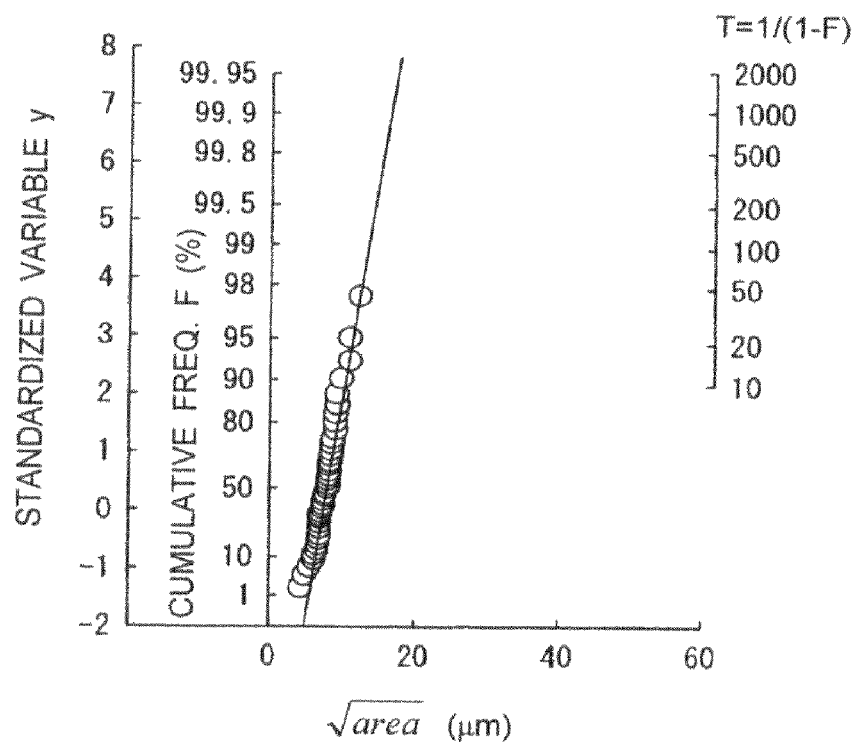
FIG. 2 is an extreme value statistical graph showing size data of nonmetallic inclusions obtained by metal microscopic observation and analyzed by an extreme value statistical method.

The size data of the largest nonmetallic inclusion obtained by the metal microscopic observation was analyzed by the extreme value statistical method. The extreme value statistical graph is shown in FIG. 2. In the graph, y is a standardized variable (y=0.711×√area−4.984), F is a cumulative frequency, and T=1/(1−F)) is a return period.

In a case of 2-dimensional inspection, this can be approximately regarded as a three-dimensional inspection for an inspection volume $V_0$ (=$S_0$×h) by providing the inspection area $S_0$ with an imaginal thickness h. As a specific method, an average value of the size of the largest nonmetallic inclusions $\sqrt{area}_{max}$ measured by the 2-dimensional inspection (=7.77× $10^{-3}$ mm) is determined and the value is assumed as an imaginal thickness h in the observation region. Accordingly, the inspection volume $V_0$ corresponding to the 2-dimensional inspection is calculated from $S_0$ and h as 0.124 $mm^3$. The validity of the approximation method is supported by theoretical analysis of Takahashi et al. (see, e.g., R. Takahashi and M. Shibuya, "Estimation of Maximum Size in Wicksell's Corpuscle Problem", Annals of the Institute of Statistical Mathematics, Vol. 50, No. 2, 1998, pp. 361-377, and R. Takahashi, M. Shibuya, "The Maximum Size of The Planar Sections of Random Spheres and Its Application to Metallurgy", Annals of the Institute of Statistical Mathematics, Vol. 48, No. 1, 1996, pp. 127-144).

Further, when chemical ingredients were analyzed for the largest nonmetallic inclusions by EDX (elemental analysis), aluminum, calcium, and sulfur were detected for 14 nonmetallic inclusions, and aluminum and sulfur were detected for one nonmetallic inclusion among nonmetallic inclusions by the number of 40. Since nonmetallic inclusions were detached, chemical ingredients could not be analyzed for remaining nonmetallic inclusions by the number of 25.

Nonmetallic Inclusion Rating by Fatigue Test

Description is to be made to a related art example of evaluating nonmetallic inclusions contained in metallic materials by a fatigue test. The evaluation method is described in Yukitaka Murakami, "Metal Fatigue, Micro-Defects and Effect of Inclusions", Yokendo, 1993, p. 94.

Figure 3:
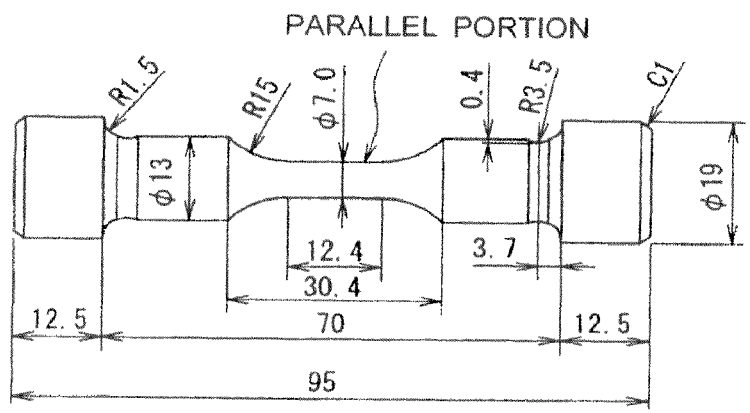
FIG. 3 is a diagram illustrating a shape and dimensions of a fatigue test specimen.

The type of the metallic material is quite identical with that used in a case of the metal microscopic observation described above and in a case of the tensile test to be described later. By using the metallic material, a fatigue test specimen of the shape and the size shown in FIG. 3 was manufactured. That is, a round bar material of 25 mm diameter was machined such that the cutting margin for the parallel portion was 1.0 mm per diameter and the cutting margin for other portions was 0.6 mm per diameter and then subjected to a heat treatment. The heat treatment includes quenching at 840° C. (oil cooling) and subsequent tempering at 240° C. (furnace cooling).

A control volume Vs including origins of fracture in the fatigue test specimen was 477 $mm^3$. Further, when Vickers hardness was measured for 20 points from the surface to the center of the parallel portion at a measuring load of 2.94 N, there was scarce variation for the hardness from the surface to the center and it was within ±2%. Further, the average value for the hardness of each fatigue test specimen was HV 682.

Then, for the fatigue test specimen subjected to the heat treatment, machining, emery polishing, and buff polishing were performed to finish the parallel portion. Then, hydrogen was charged to a portion of fatigue test specimens by immersing them into an aqueous solution of ammonium thiocyanate of 20 mass % concentration at 40° C. for 48 hours. Then, flaws formed by hydrogen charge was removed by emery polishing and buff polishing to the parallel portion to finish the same.

A fatigue test (dynamic test) was carried out to the thus obtained fatigue test specimens (seven types) to fracture the parallel portions. The fracture test was carried out in laboratory air by using a hydraulic servo-assisted tensile-compression fatigue testing machine at a cyclic frequency f of from 50 to 75 Hz, and at a stress ratio R of −1 (tensile stress and compressive stress were identical). In the tensile-compression fatigue test, when a bending stress exerts on a test portion, somewhat lower fatigue strength tends to be obtained. Accordingly, strain gages were attached to positions of dividing the circumference near a grip portion into quarters on every test specimen and the test specimen was attached to the fatigue testing machine while adjusting carefully so that the bending stress did not exert on the test portion upon loading a stress.

For the hydrogen charged fatigue test specimen, the time from the end of the hydrogen charge to the start of the fatigue test was defined as three hours. Further, just after completion of the fatigue test, the amount of hydrogen in the fatigue test specimen was measured. The amount of hydrogen was measured by thermal desorption spectroscopy (TDS). That is, a disk-like specimen of 7.0 mm diameter and 2.0 μmm thickness was cut out from the parallel portion of the fatigue test specimen, and the amount of desorbed hydrogen was measured by elevating a temperature to 573 K/s at a temperature elevation rate of 0.5 K/s. The result is shown in Table 1.

TABLE 1

| Test Specimen No. | Hydrogen Charge | Applied Stress (Mpa) | Fracture Life (cycles) | Type of Nonmetallic Inclusion | √area (μm) | Hydrogen Amount (wppm) |
|---|---|---|---|---|---|---|
| 1 | No | 800 | $4.3 \times 10^7$ | Al type (Al, Ca, Si, S) | 17.0 | 0.11 |
| 2 | No | 850 | $2.0 \times 10^7$ | Not fractured | 18.8 | 0.12 |
| 2* | No | 950 | $4.9 \times 10^6$ | Al type (Al) | — | — |
| 3 | No | 900 | $3.9 \times 10^6$ | Al type (Al, Ca, S) | 11.3 | 0.08 |
| 4 | Yes | 650 | $8.3 \times 10^5$ | Al type (Al, Ca, S) | 15.5 | 2.03 |
| 5 | Yes | 700 | $1.4 \times 10^4$ | Al type (Al, Ca, Si, S) | 25.7 | 3.00 |
| 6 | Yes | 550 | $5.8 \times 10^5$ | Al type (Al, Ca, S) | 22.8 | 2.76 |
| 7 | Yes | 600 | $7.6 \times 10^5$ | Al type (Al) | 15.8 | 2.97 |

When the parallel portion of the fatigue test specimen was fractured by the fatigue test, the entire surface vertical to the direction of the main stress (direction of tensile stress) of the fatigue test was observed. That is, the fracture surface was put to SEM observation and the size of the nonmetallic inclusions as origins of fracture (square root of projected area √area as viewed in the direction of the main stress in the fatigue test) was measured. Then, the nonmetallic inclusions were identified by EDX attached to SEM. The acceleration voltage in SEM observation and EDX analysis was 20 kV.

Table 1 shows the loaded stress, fracture life (number of stress cycles till fracture of the fatigue test specimen), the type of nonmetallic inclusion as origins of fracture (elements of nonmetallic inclusions are shown in the brackets), the square root of projected area √area of nonmetallic inclusion, and the amount of hydrogen in the fatigue test specimen after the fatigue test. The test specimen No. 2* shows the result of putting a fatigue test specimen No. 2 which was not fractured till the number of stress cycles of $2×10^7$ at a loaded stress of 850 MPa successively to the fatigue test at a loaded stress of 950 MPa.

Irrespective of the hydrogen charge, the fatigue test specimen was fractured at the nonmetallic inclusion as the origin. Typical fish eyes were observed at the fracture surface of the fracture fatigue test specimen and a nonmetallic inclusion was present at the center thereof. The shape of the fish eye was substantially circular. Since aluminum and calcium were detected mainly as the chemical ingredients of the nonmetallic inclusion, it is considered that the nonmetallic inclusions is $Al_2O_3 \cdot (CaO)_x$.

Figure 4:
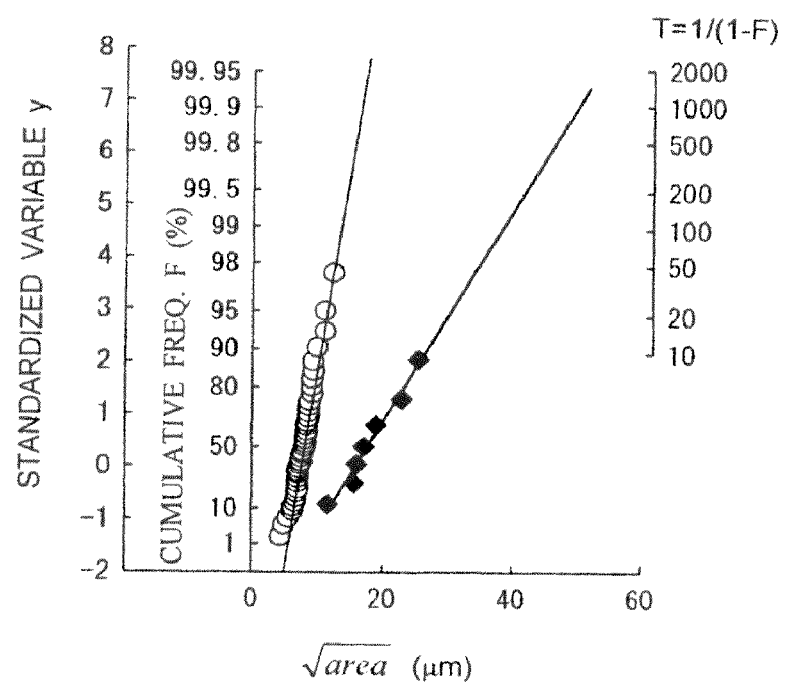
FIG. 4 is an extreme value statistical graph showing size data of nonmetallic inclusions obtained by a fatigue test and analyzed by an extreme value statistical method.

The data for the size of the nonmetallic inclusions $\sqrt{area}$ as the origins of fracture obtained by the fatigue test as described above was analyzed by the extreme value statistical method. FIG. 4 shows an extreme value statistical graph (plotted by black square marks). In the graph, y is a standardized variable ($y=0.194×\sqrt{area}−3.030$), F is a cumulative frequency, and T is a return period. The inspection volume $V_0$ in this case is a volume for the parallel portion of the fatigue test specimen. That is, the control volume Vs of the fatigue test specimen is 477 mm³.

Figure 5:
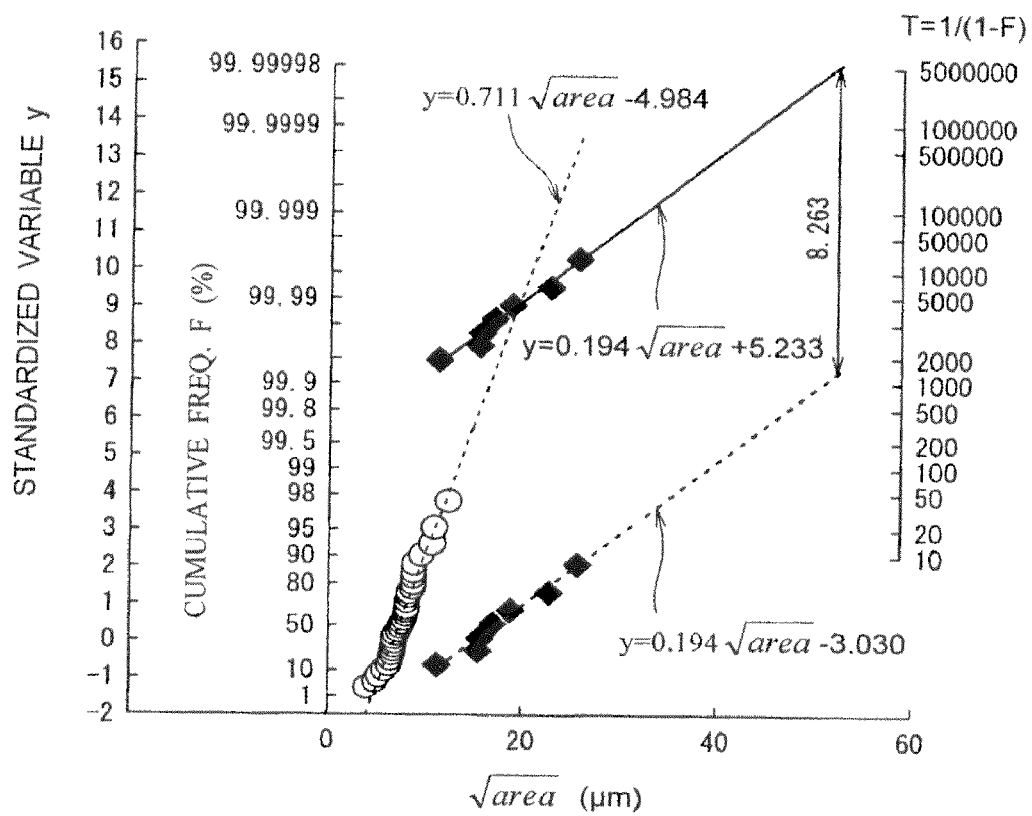
FIG. 5 is a graph obtained by converting the extreme value statistical graph of FIG. 4.

In the graph, an extreme value statistical graph obtained by the metal microscopic observation shown in FIG. 2 (plotted by circle marks) is also shown together. The inspection volume $V_0$ in the case of the metal microscopic observation is 0.124 mm³. In a case where the values of the inspection volume $V_0$ are different as described above, the extreme value statistical data can be evaluated by conversion based on the inspection volume $V_0$ of the reference sample. Then, when the nonmetallic inclusions as the origins of fracture by the fatigue test are evaluated by conversion based on the inspection volume $V_0$, it is as shown in the graph of FIG. 5. That is, the linear line of the extreme value statistical graph forms a linear line displaced in parallel by $\ln(V_s/V_0)$, and $\ln(V_s/V_0)$ in this case is 8.236.

It is considered that the slopes of the two linear lines in the extreme value statistical graph are different because the types (components) are different between the nonmetallic inclusions as the origin of fracture in the fatigue test and the nonmetallic inclusions observed by the metal microscopic observation. It is also pointed out in the Non-patent document 5 that slopes of both of the linear lines are different. For estimating the nonmetallic inclusion as the origin in the fatigue test from the evaluation by the metal microscopic observation, it is necessary to observe a large area having an inspection area $S_0$ of 15.9 mm² or more. Accordingly, it is considered that finding of large nonmetallic inclusions as the origin of fracture by the metal microscopic observation is not always easy and it is expensive as well.

Nonmetallic Inclusion Rating by Tensile Test

Description is to be made to an example of the invention of evaluating nonmetallic inclusions contained in a metallic material by a tensile test.

The type of the metallic material is quite identical with that used in the case of the metal microscopic observation and the fatigue test described above. By using the metallic material, a tensile test specimen of the shape and the size as shown in FIG. 1 was manufactured. That is, after machining a round bar material of 25 mm diameter such that the cutting margin was 1.0 mm for the parallel portion per diameter and the cutting margin for other portions was 0.6 mm per diameter, a heat treatment was applied under one of the following five conditions.

Condition A: After keeping in an RX gas atmosphere at 840° C. and quenching by oil cooling, the specimen was kept at 240° C. for 2 hours and then tempered by furnace cooling.

Condition B: After keeping in an RX gas atmosphere at 840° C. and quenching by oil cooling, the specimen was kept at 300° C. for 2 hours and then tempered by furnace cooling.

Condition C: After keeping in an RX gas atmosphere at 840° C. and quenching by oil cooling, the specimen was kept at 370° C. for 2 hours and then tempered by water cooling.

Condition D: After keeping in an RX gas atmosphere at 840° C. and quenching by oil cooling, the specimen was kept at 470° C. for 2 hours and then tempered by water cooling.

Condition E: After keeping in an RX gas atmosphere at 840° C. and quenching by oil cooling, the specimen was kept at 550° C. for 2 hours and then tempered by oil cooling.

The control volume Vs as the origin of fracture of the tensile test specimen was 477 mm³. Further, when the Vickers hardness was measured at 20 points from the surface to the center of the parallel portion under a measuring load of 2.94N, the hardness was scarcely scattered from the surface to the center and it was within ±3%. Further, the average value for the hardness of each of the tensile test specimens was HV 678 (scattering within ±2%) in a case where the condition for the heat treatment was the condition A, HV 611 in a case where the condition for the heat treatment was the condition B (scattering within ±2%), HV 559 in a case where the condition for the heat treatment was the condition C (scattering within ±3%), HV 447 in a case where the condition for the heat treatment was the condition D (scattering within ±2%), and in a case where the condition for the heat treatment was the condition E HV 346 (scattering within ±3%).

Then, the tensile test specimen subjected to the heat treatment was put to machining, emery polishing and buff polishing to finish the parallel portion. Then, a portion of the tensile stress test specimens was charged with hydrogen by immersing them in an aqueous solution of at a concentration ammonium thiocyanate of 1 mass % or 20 mass % at 40° C. for 48 hours (concentration of the aqueous solution of ammonium thiocyanate for hydrogen charge is sometimes referred to hereinafter as concentration at hydrogen charge). Then, the parallel portion was put to emery polishing and buff polishing to remove the flaws formed by hydrogen charge to finish the same.

A tensile test (static test) was carried out to the thus obtained tensile test specimens (24 types) to fracture the parallel portions. The tensile test was carried out in laboratory air at a room temperature, and the tensile speed (cross head speed V) was 0.05 mm/min, 1 mm/min, or 100 mm/min. Since the tensile test is carried out in laboratory air at a room temperature, it is considered that the amount of hydrogen contained in the tensile test specimen is different for the tensile test specimen charged with hydrogen depending on the time from the completion of the hydrogen charge to the initiation of the tensile test. Then, the time from the completion of the hydrogen charge to the initiation of the tensile test (leaving time) was made uniform as 2 hours, so that the amount of hydrogen contained in the tensile test specimens upon initiation of the tensile test was substantially identical for each of the tensile test specimens.

Further, from the completion of the hydrogen charge to the initiation of the tensile test, the amount of hydrogen was changed by leaving the specimens in laboratory air at a room temperature for 24 hours, 72 hours, 150 hours, or 200 hours, and the relation between the tensile strength and the form of fracture and the amount of hydrogen was examined for the tensile test specimens.

For the hydrogen charged tensile test specimens, the amount of hydrogen in the tensile test specimens was measured immediately after the completion of the tensile test. The hydrogen amount was measured by a temperature desorption spectroscopy (TDS) using a quadrupole mass spectrometer. That is, a disk-like specimen of 4.5 mm diameter and 2.0 mm thickness was cut out from the parallel portion of the tensile test specimen, and the temperature was elevated to 573K at a temperature elevation rate of 0.5K/s, and the amount of desorped hydrogen was measured. The results are shown in Table 2.

and the size of the nonmetallic inclusions as the origins of fracture (square root of the projected area $\sqrt{area}$ as viewed from the direction of the tensile axis of the tensile test). Then, the nonmetallic inclusions were identified by EDX attached to SEM. The acceleration voltage in SEM observation and EDX analysis was 20 kV.

Table 2 shows the tensile speed, the tensile fracture strength, the strain, the hydrogen charge concentration, the leaving time (time from the completion of hydrogen charge to the initiation of the tensile test), the amount of hydrogen in the tensile test specimen after the tensile test, the type of the

TABLE 2

| | Test Specimen No. | Hydrogen Charge | Hydrogen Charge Concentration (mass %) | Hardness (HV) | Tensile Strength (MPa) | Strain (%) | Hydrogen Amount (wppm) | Tensile Speed (mm/min) | Leaving Time (hours) | $\sqrt{area}$ (μm) | Type of Nonmetallic Inclusion |
|---|---|---|---|---|---|---|---|---|---|---|---|
| Examples | 1 | Yes | 20 | 678 | 1179 | 0.57 | 2.10 | 1 | 2 | 12.1 | Al type (Al, Ca, S) |
| | 2 | Yes | 20 | 678 | 1268 | 0.53 | 2.72 | 1 | 2 | 19.1 | Al type (Al, Ca) |
| | 3 | Yes | 20 | 678 | 996 | 0.51 | 4.25 | 1 | 2 | 13.2 | Al type (Al, Ca, S) |
| | 4 | Yes | 20 | 678 | 1266 | 0.60 | 2.57 | 1 | 24 | 14.2 | Al type (Al, Ca, S) |
| | 5 | Yes | 20 | 678 | 1402 | 0.49 | 1.80 | 1 | 72 | 11.5 | Al type (Al, Ca, S) |
| | 6 | Yes | 20 | 678 | 1494 | 0.74 | 0.72 | 1 | 200 | 23.9 | Al type (Al, Ca) |
| | 7 | Yes | 20 | 678 | 1568 | 0.66 | 0.64 | 1 | 200 | 12.4 | Al type (Al, Ca, S) |
| | 8 | Yes | 20 | 678 | 952 | 0.44 | 2.09 | 0.05 | 2 | 19.0 | Al type (Al, Ca, S) |
| | 9 | Yes | 20 | 678 | 1212 | 0.55 | 2.54 | 50 | 2 | 31.9 | Al type (Al, Ca) |
| | 10 | Yes | 20 | 678 | 1148 | 0.52 | 4.52 | 100 | 2 | 21.3 | Al type (Al) |
| | 11 | Yes | 1 | 678 | 1478 | 0.68 | 1.13 | 1 | 2 | 19.6 | Al type (Al) |
| | 12 | Yes | 1 | 678 | 1501 | 0.69 | 0.32 | 1 | 150 | 12.8 | Al type (Al, Ca, S) |
| | 13 | Yes | 20 | 611 | 1037 | 0.46 | 2.50 | 1 | 2 | 23.1 | Al type (Al, Ca, S) |
| | 14 | Yes | 20 | 559 | 1598 | 0.77 | 1.74 | 1 | 2 | 13.0 | Al type (Al, Ca, S) |
| | 15 | Yes | 20 | 447 | 1421 | 0.66 | 2.05 | 1 | 2 | 13.1 | Al type (Al, Ca, S) |
| Comparative Examples | 1 | Yes | 20 | 346 | 1123 | 7.60 | 1.07 | 1 | 2 | — | Matrix |
| | 2 | No | — | 678 | 2422 | 2.22 | 0.01 | 1 | — | — | Surface |
| | 3 | No | — | 678 | 2409 | 2.29 | 0.03 | 1 | — | 9.9 | Ti type (Ti) |
| | 4 | No | — | 678 | 2523 | 2.09 | 0.02 | 1 | — | 10.9 | Ti type (Ti) |
| | 5 | No | — | 611 | 2024 | 1.14 | ≦0.01 | 1 | — | 11.0 | Ti type (Ti) |
| | 6 | No | — | 559 | 1928 | 2.68 | ≦0.01 | 1 | — | 9.6 | Ti type (Ti) |
| | 7 | No | — | 447 | 1797 | 1.38 | ≦0.01 | 1 | — | 9.5 | Ti type (Ti) |
| | 8 | No | — | 346 | 1123 | 10.4 | ≦0.01 | 1 | — | — | Matrix |
| | 9 | No | — | 346 | 1124 | 11.0 | ≦0.01 | 1 | — | — | Matrix |

Then, the hydrogen releasing property of the hydrogen charged tensile test specimens was investigated. For the investigation of the hydrogen releasing property, a round bar test specimen formed of the metallic materials described above (4.5 mm diameter, 100 mm length) was used. Then, after the heat treatment and the hydrogen charge, the amount of hydrogen was measured by a temperature desorption gas spectroscopy using a quadrupole mass spectrometer in the same manner as described above. The temperature was elevated to 573K at a temperature elevation rate of 0.5K/s. The concentration of hydrogen charge was 20 mass %.

Figure 6:
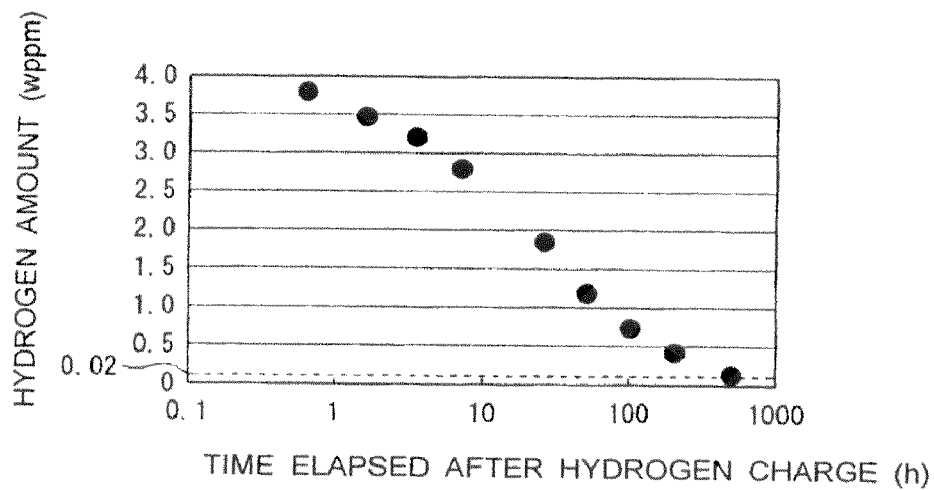
FIG. 6 is a graph showing a hydrogen releasing property of a tensile test specimen.
Figure 7:
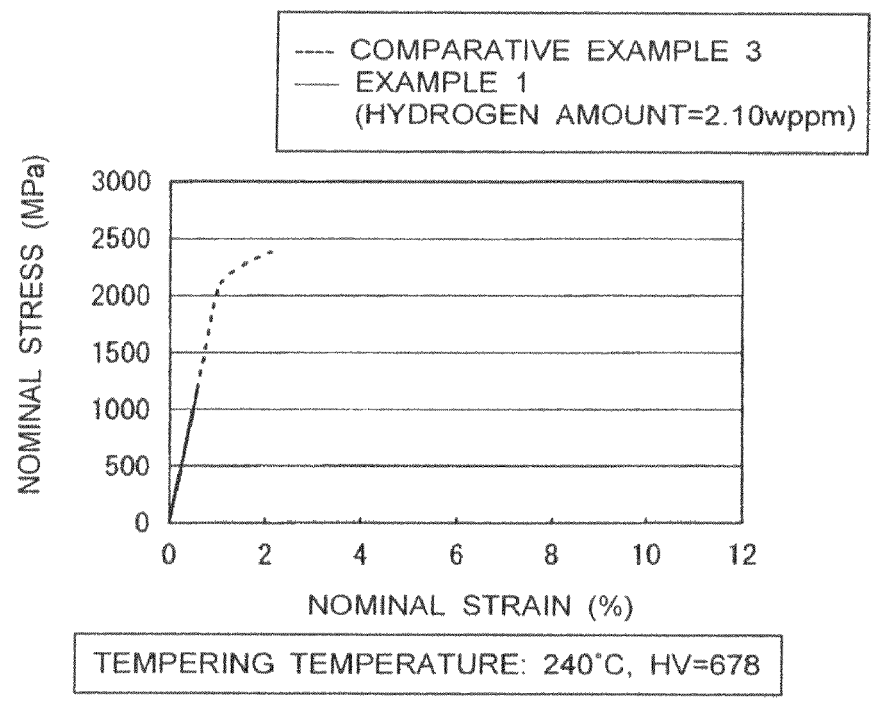
FIG. 7 is a graph showing an example of a nominal stress-strain curve.
Figure 8:
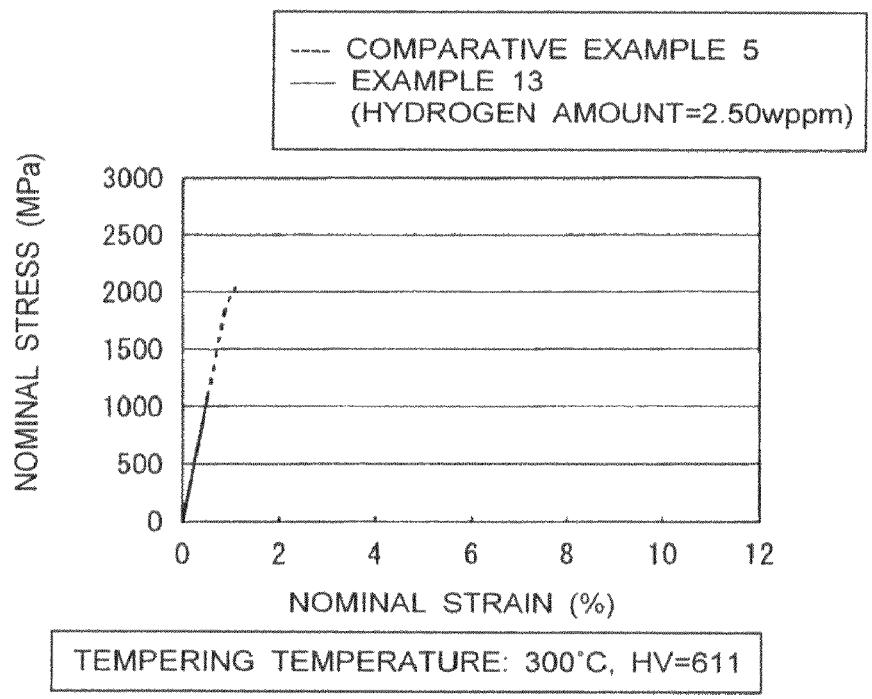
FIG. 8 is a graph showing another example of a nominal stress-strain curve.
Figure 9:
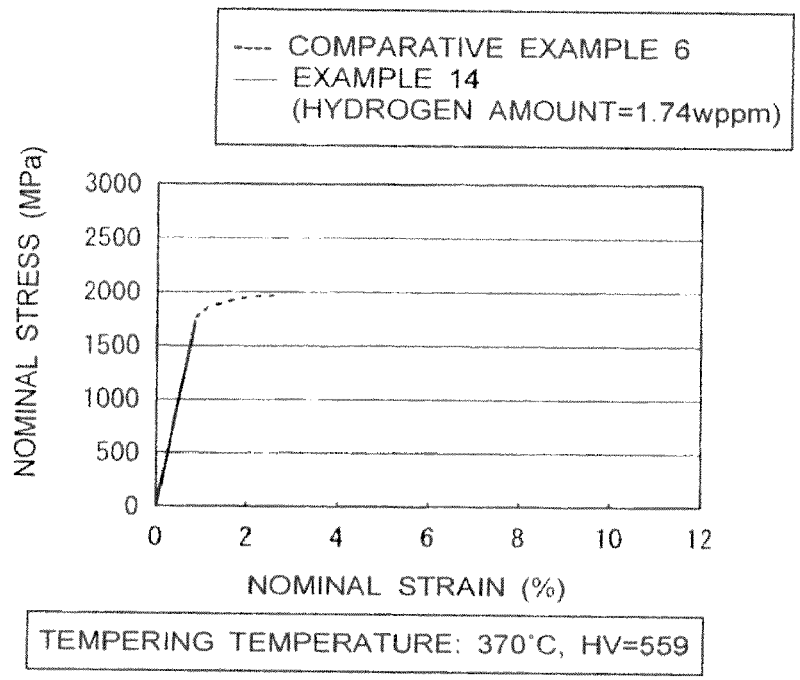
FIG. 9 is a graph showing yet another example of a nominal stress-strain curve.
Figure 10:
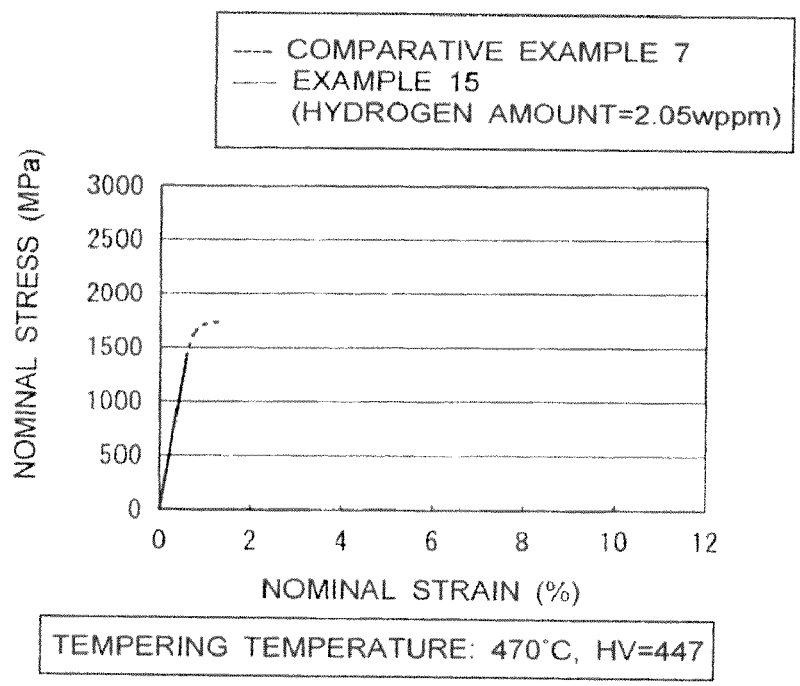
FIG. 10 is a graph showing yet another example of a nominal stress-strain curve.
Figure 11:
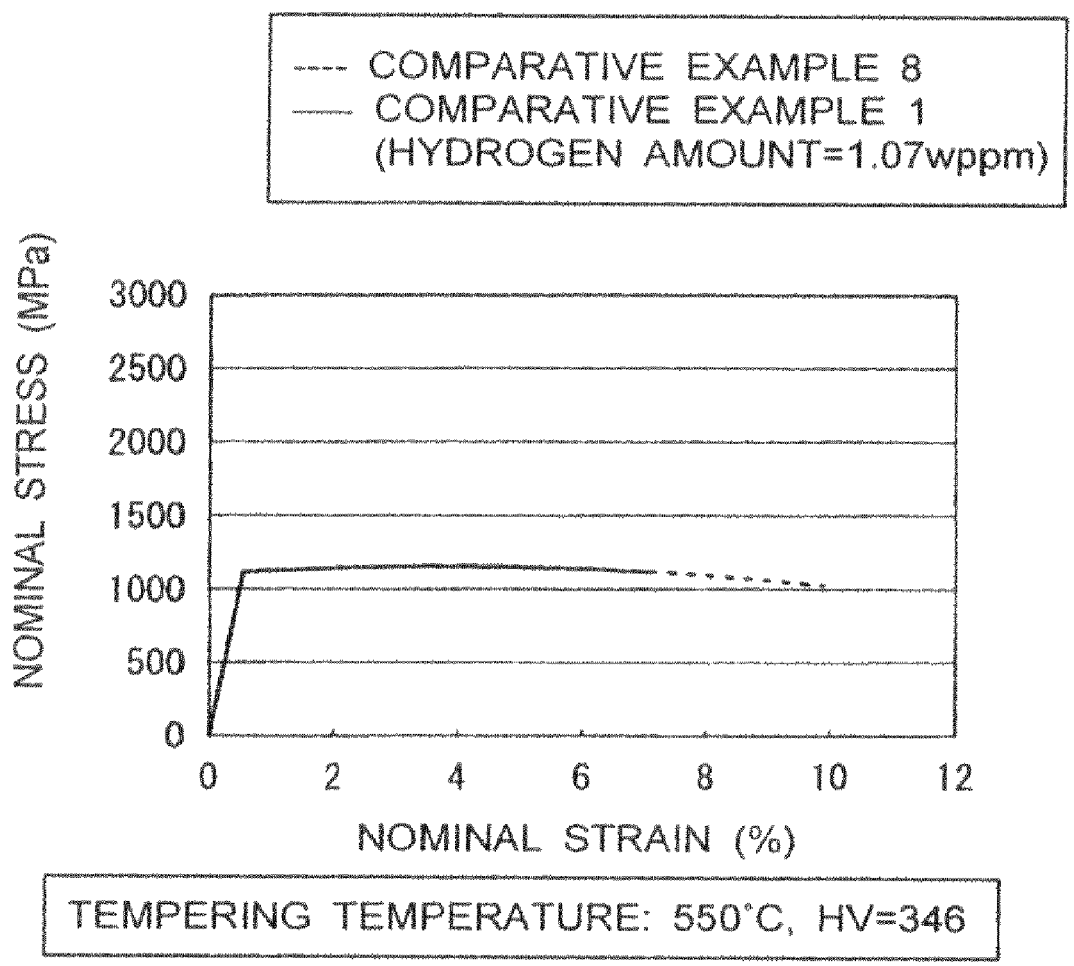
FIG. 11 is a graph showing yet another example of a nominal stress-strain curve.

For examining the hydrogen releasing property at a normal temperature, a chip specimen of 2.0 mm thickness was cut out from the hydrogen charged round bar test specimen on every lapse of a predetermined time and the amount of hydrogen was measured. The chip specimen was cut out at a position apart by 4.5 mm or more from the end face of the round bar test specimen. The amount of hydrogen in the round bar test specimen under the heat treatment condition A is shown in the graph of FIG. 6. As can be seen from the graph, the amount of hydrogen was lowered monotonously as the time lapsed from the completion of the hydrogen charge. The hydrogen amount in the not hydrogen charged round bar test specimen was 0.02 wppm.

When the parallel portion of the tensile test specimen was fractured by the tensile test, the entire surface vertical to the direction of the tensile axis (direction of tensile stress) was observed. That is, the fracture surface was observed by SEM nonmetallic inclusions as the origins of fracture (elements constituting nonmetallic inclusions are shown in the brackets), and the square root of the projected area $\sqrt{area}$ of the nonmetallic inclusion. For comparative examples 1, 2, 8, and 9, since the origins of fracture were not at the nonmetallic inclusions but in the matrix or on the surface of the tensile test specimen, "matrix" or "surface" as the origins of fracture are described in the column for the type of the nonmetallic inclusion forming the origins of fracture.

FIGS. 7 to 11 show examples of nominal stress-nominal strain curves in the examples and the comparative examples. In this case, the time from the completion of the hydrogen charge to the initiation of the tensile test was 2 hours and the tensile speed was 1 mm/min in each of the drawings. While they are compared for those under identical heat treatment conditions and having identical hardness, in each of the drawings, curves of comparative examples in FIGS. 7 to 10 at a hardness HV of 678, 611, 559, and 447 were fractured in a plastic region after yielding, whereas the curves of the examples were fractured in an elastic region. Accordingly, the tensile fracture strength for each of the examples is lower than the tensile fracture strength of the comparative example not subjected to the hydrogen charge. On the other hand, curves for both comparative examples at a hardness of HV 346 in FIG. 11 were not fractured in the elastic region and the tensile fracture strength was substantially identical and the strength was not lowered by the hydrogen charge.

As can be seen from Table 2, hydrogen charged specimens examples 1 to 15 had a hardness of HV 400 or more, and fractured at the nonmetallic inclusions as the origins. Since aluminum and calcium were mainly detected as the chemical ingredients of the nonmetallic inclusions, it is considered that the nonmetallic inclusions are $Al_2O_3 \cdot (CaO)_x$.

Figure 12:
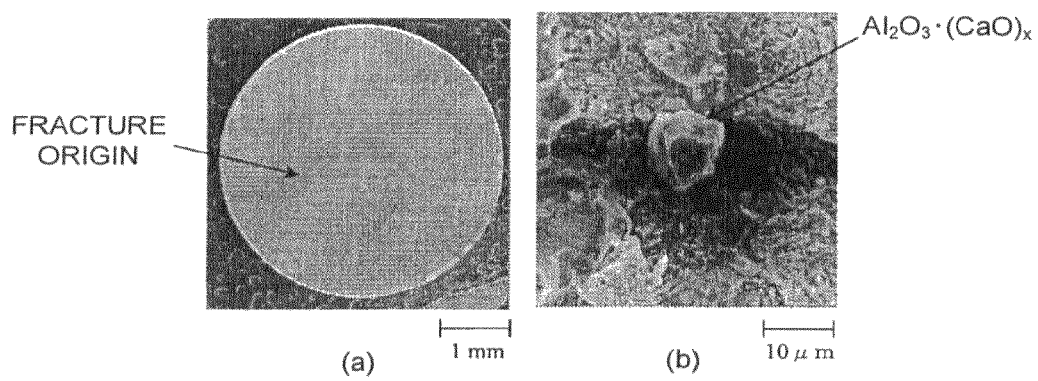
FIG. 12 is an enlarged microscopic photograph obtained by observing a fracture surface of a tensile test specimen of Example 1.
Figure 13:
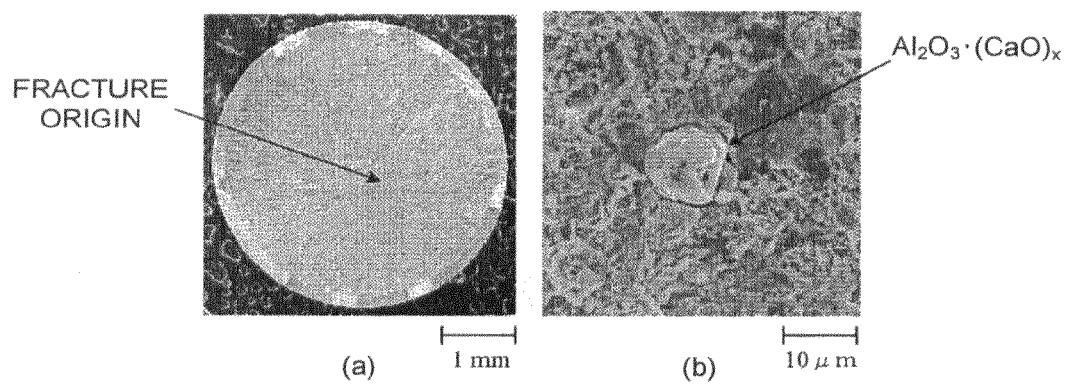
FIG. 13 is an enlarged microscopic photograph obtained by observing a fracture surface of a tensile test specimen of Example 14.

FIG. 12 shows an enlarged microscopic views observing the fracture surface of the tensile test specimens of Example 1, and FIG. 13 shows enlarged microscopic views observing the fracture surface of the tensile test specimen of Example 14. In each of the figures, (a) is an entire view of fracture surface and (b) is an enlarged view for the origin of fracture and the peripheral portion thereof in (a).

It can be seen from the photographs that the fracture extends radially from the nonmetallic inclusion as the origin. Further, in view of (b) in FIG. 12 and (b) in FIG. 13, the size of the nonmetallic inclusion as the origin of fracture, that is, the largest nonmetallic inclusion in the control volume can be measured.

While the tensile test specimen of Comparative Example 1 was hydrogen charged, the tensile test specimen caused cup and cone type fracture and the nonmetallic inclusions as the origin of fracture could not be identified from the result of observation of fracture surface.

Figure 14:
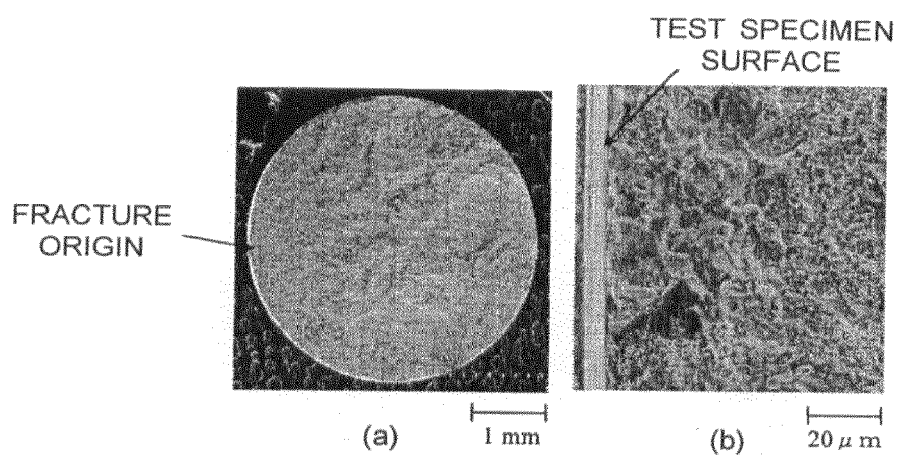
FIG. 14 is an enlarged microscopic photograph obtained by observing a fracture surface of a tensile test specimen of Comparative Example 2.
Figure 15:
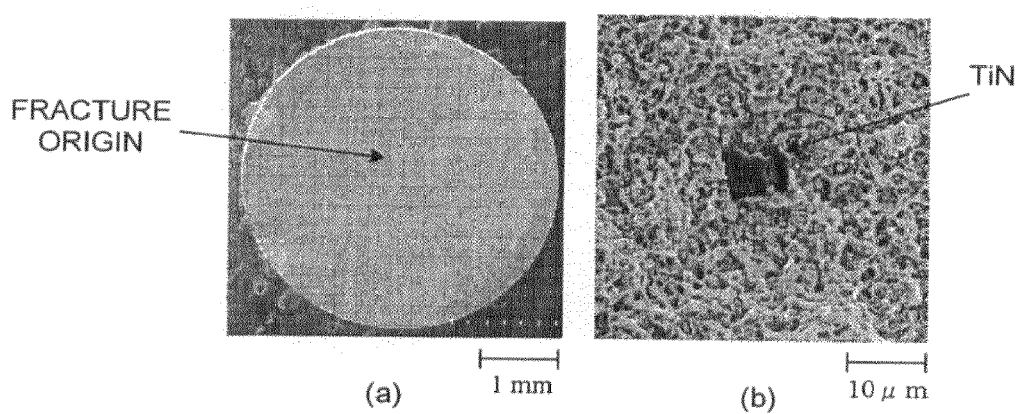
FIG. 15 is an enlarged microscopic photograph obtained by observing a fracture surface of a tensile test specimen of Comparative Example 6.

Further, the tensile test specimens of Comparative Examples 2 to 9 were not hydrogen charged and the amount of hydrogen in the tensile test specimen was 0.03 wppm or less. For Comparative Examples 2 to 9, five specimens were fractured from the nonmetallic inclusions as origins, while one specimen was fractured at the surface of the tensile test specimen as the origin and three specimens were fractured in the matrix of the tensile test specimen as the origin. Since Ti was detected as the chemical ingredient of the nonmetallic inclusion, it is considered that the nonmetallic inclusion is TiN. FIG. 14 shows an enlarged microscopic view observing the fracture surface of Comparative Example 2 fractured on the surface of the tensile test specimen as the origin. FIG. 15 is an enlarged microscopic view observing the fracture surface of Comparative Example 6 fractured from the TiN type nonmetallic inclusion as the origin.

Figure 16:
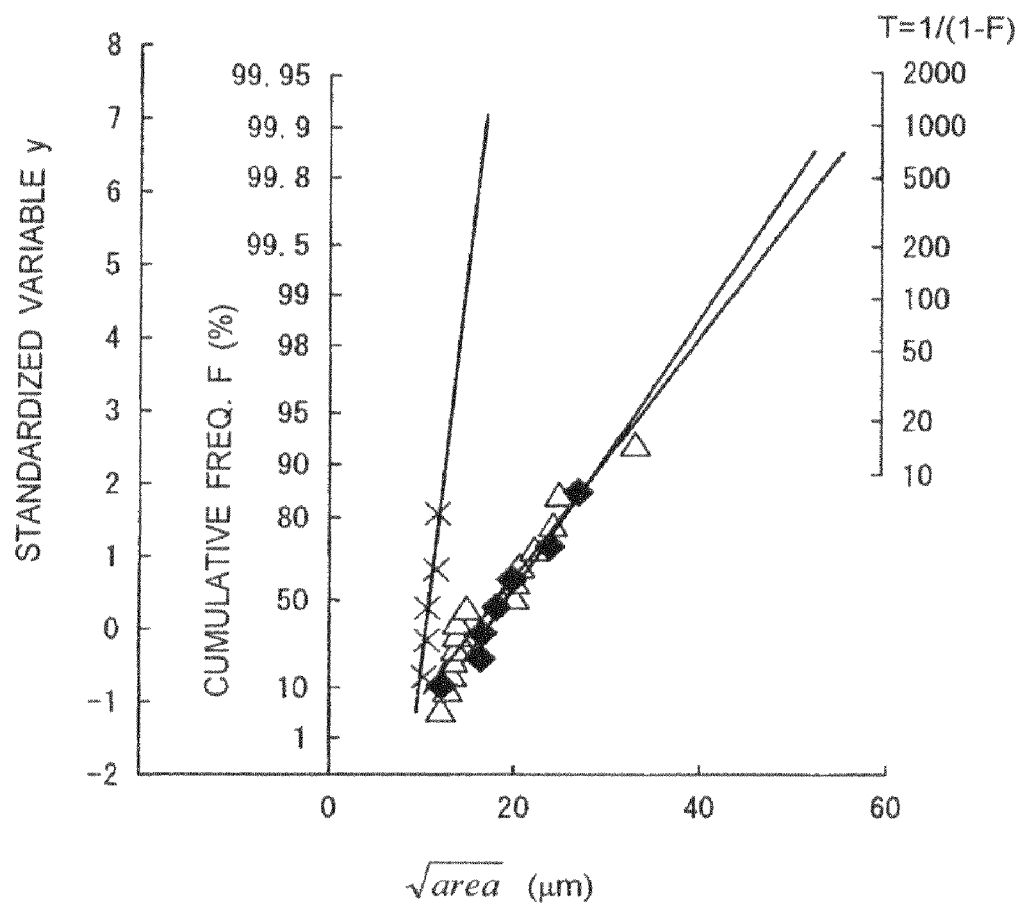
FIG. 16 is an extreme value statistical graph showing size data of nonmetallic inclusions obtained by a tensile test and analyzed by an extreme value statistical method.

Data for the size of the nonmetallic inclusions as the origins of fracture (square root of projected area $\sqrt{area}$) obtained by the tensile test for the tensile test specimens of Examples 1 to 15 were analyzed by the extreme value statistical method. FIG. 16 shows an extreme value statistic graph. Examples are plotted by trigonal marks and comparative examples are plotted by × marks. In the graph, y is a standardized variable, F is a cumulative frequency, and T is a return period. The standardized variable of the example is: $y=0.1730 \times \sqrt{area} - 2.4879$. The standardized variable of the comparative example is: $y=1.1577 \times \sqrt{area} - 11.326$. Since the ingredients of the nonmetallic inclusions as the tensile fracture origins are different between the examples and the comparative examples. Extreme value statistic graphs do not conform to each other. The inspection volume $V_0$ in this case is a volume for the parallel portion of the tensile test specimen. That is, in the tensile test specimen, the control volume Vs is 477 mm³. In the graph, an extreme value statistic graph obtained by the fatigue test shown in FIG. 4 (plotted by square marks) is shown together.

As can be seen from the graph of FIG. 16, the extreme value statistic graph obtained by the tensile test and the extreme value statistic graph obtained by the fatigue test are substantially identical with each other. When the size of the largest nonmetallic inclusion: $\sqrt{area}_{max}$ as the origin of fracture among the nonmetallic inclusions in the control volume Vs (=477 mm³) of the test specimen is estimated by using the return period T(N) of the graph and the distribution line obtained by the tensile test in FIG. 16, it was 27.7 μm for the test specimens by the number of 10 and 41.0 μm for the test specimens by the number of 100.

On the contrary, when estimation is carried out in the same manner by using the return period T(N) and the distribution line obtained by the fatigue test, the size was 27.6 μm in a case where the number of test specimen was 10 and 39.5 μm in a case where the number of the test specimen was 100. In view of the results, it can be seen that the result obtained by the fatigue test, that is, the size of the largest nonmetallic inclusion among the nonmetallic inclusions in the metallic material can be estimated at a good accuracy by carrying out the tensile test for the hydrogen charged tensile test specimen and analyzing the data for the size of the nonmetallic inclusions as the origin of fracture.

Then, a relation between the tensile strength and the amount of hydrogen was examined for Examples 1 to 7, 11, and 12, and Comparative Examples 2 to 4. The condition for the heat treatment of the tensile test specimens are the condition A. Further, the tensile test specimens of Examples 1 to 7, 11, and 12 were subjected to the hydrogen charge, whereas the tensile test specimens of Comparative Examples 2 to 4 were not subjected to the hydrogen charge. Further, in Examples 1 to 7, 11, and 12, the amount of residual hydrogen in the tensile test specimens was changed by changing the time from the completion of hydrogen charge to the initiation of the tensile test (leaving time) variously.

Figure 17:
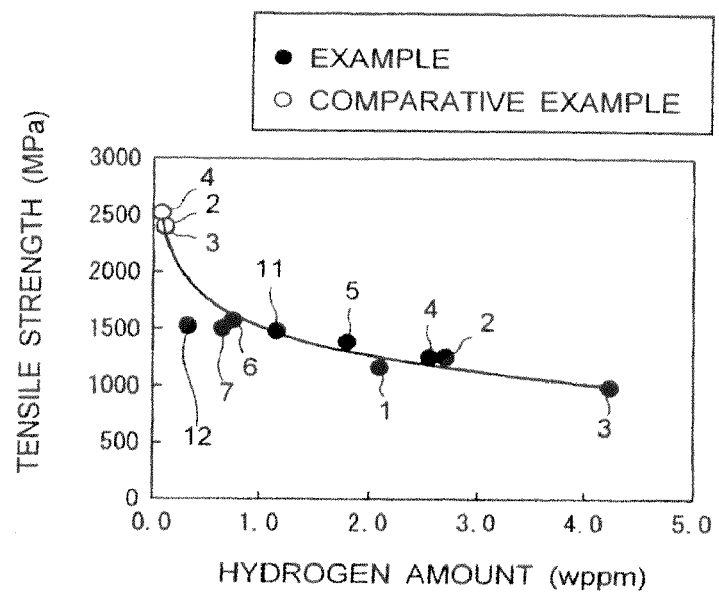
FIG. 17 is a graph showing a relation between tensile strength and amount of hydrogen.

From the graph in FIG. 17, it can be seen that the tensile strength is lowered by the hydrogen charge and it is estimated therefrom that fracture tends to occur from the nonmetallic inclusions as the origin under the effect of hydrogen.

Onishi and Kaga performed a creep type low load test under a high pressure hydrogen atmosphere by using AISI 4340 steels while varying the strength from 1160 MPa to 1570 MPa by changing the tempering temperature and showed that the fracture strength was lowered along with increase of the hydrogen pressure and the fracture strength lowered remarkably as the strength was higher. Further, they investigated the hydrogen amount and showed that it was 0.14 wppm at the hydrogen pressure of 3 MPa, 0.13 wppm at the hydrogen pressure of 5 MPa, and 0.23 wppm at the hydrogen pressure of 10 MPa (see, e.g., Keizo Onishi and Hisashi Kaga, "Room Temperature Hydrogen Gas Embrittlement of Structural Steel", Tetsu-to-Hagane, The Iron and Steel Institute of Japan, Vol. 69, No. 2, 1983, pp. A136-A139).

According to the examples of the invention, when a tensile test is carried out with 0.32 wppm of hydrogen in the tensile test specimen, fracture occurs at the nonmetallic inclusion as the origin to lower the strength. Accordingly, it is considered in view of the reports of Onishi and Kaga that when a tensile test is carried out with 0.2 wppm or more of hydrogen in the tensile test specimen, fracture occurs at the nonmetallic inclusion as the origin to lower the strength. The amount of hydrogen in the tensile test specimen is preferably 0.2 wppm or more, more preferably, 0.3 wppm or more (or 0.32 wppm or more) and, further preferably, 0.6 wppm or more (or 0.64 wppm or more).

Further, for Examples 1 to 3, Example 13, Example 14, and Comparative Example 1, the ratio of the tensile strength before and after the hydrogen charge (tensile strength after hydrogen charge/tensile strength before hydrogen charge) was calculated and relation between the tensile strength ratio and the hardness of the tensile test specimen was examined. The hardness of the tensile test specimen was controlled depending on the conditions of the heat treatment.

Figure 18:
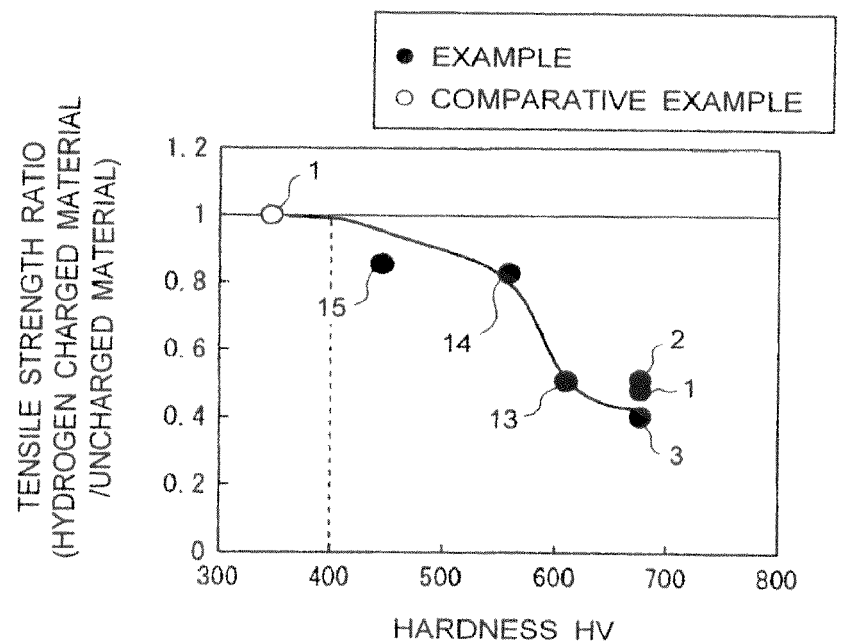
FIG. 18 is a graph showing a relation between a tensile strength ratio and hardness of tensile test specimens.

It can be seen from the graph in FIG. 18 that the tensile strength is lowered as the hardness of the tensile test specimen is higher. Fukui et al. determined the ratio of a bending stress to a static bending strength not causing delayed fracture for 30 hours or more in an aqueous solution of hydrogen chloride (hereinafter referred to as a delay fracture strength ratio) using low alloy steels while changing the tempering temperature, and showed that the delayed fracture strength ratio was lowered remarkably when the hardness of the tensile test specimen was HRC 40 (HV 375) or higher.

Further, Fujita et al. determined the tensile fracture strength in a case of using low alloy steels and immersing them in water for 100 hours, and reported that when the hardness of the tensile test specimen was HV 400 or more the tensile fracture strength in a case of immersing in water for 100 hours was lower than the tensile fracture strength in laboratory air (see, e.g., T. Fujita and Y. Yamada, "Physical Metallurgy and SCC in High Strength Steels", 1977, p. 736, NZCE-5).

According to the examples of the invention, the effect of hydrogen is different between a tensile test specimen at a hardness of HV 366 and a tensile test specimen at a hardness of HV 447 or more. That is, in the tensile test specimens having a hardness of HV 366, the tensile fracture strength is about the same irrespective the hydrogen charge. On the other hand, in the tensile test specimens having a hardness of HV 447 or more, hydrogen accelerates fracture at the nonmetallic inclusions as the origins and lowers the tensile fracture strength.

Accordingly, based on the report of Fukui et al. and Fujita et al., since it is considered that occurrence of fracture originating from the nonmetallic inclusion is facilitated by the effect of hydrogen when the hardness of the tensile test specimen is HV 400 or more, the hardness of the tensile test specimen is, more preferably, HV 450 or more and, further preferably, HV 500 or more for stable evaluation of the nonmetallic inclusions.

While the present invention has been described with reference to exemplary embodiments and examples thereof, the scope of the present invention in not limited to the exemplary embodiments and examples described above, and it will be understood by those skilled in the art that various changes and modifications may be made therein with out departing from the sprit and scope of the present invention.

Some aspects of the present invention are described in Shinji Fujita, Saburo Matsuoka and Yukitaka Murakami, "A New Inclusion Rating Method by the Tensile Test with Hydrogen-precharged Specimens", Tetsu-to-Hagane, The Iron and Steel Institute of Japan, Vol. 95, No. 12, December 2009, pp. 870-879, the entire content of which is incorporated herein by reference.

What is claimed is:

1. An inclusion rating method using a tensile test, the method comprising the steps of:
   actively charging a test specimen made of metallic material with hydrogen such that an amount of hydrogen in the test specimen is 0.2 wppm or more;
   carrying out the tensile test on the test specimen to cause a fracture originating from a nonmetallic inclusion affected by hydrogen in the test specimen;
   identifying a type of the nonmetallic inclusion;
   measuring a size of the nonmetallic inclusion; and
   evaluating a cleanliness of the metallic material by obtaining a distribution function of the size of the nonmetallic inclusion; wherein the step off measuring the size of the nonmetallic inclusion comprises measuring a projected area of the nonmetallic inclusion projected in a direction of a tensile axis of the tensile test, and wherein the step of evaluating the cleanliness of the metallic material comprises analyzing a square root of the projected area using an extreme value statistics, and estimating the size of the largest nonmetallic inclusion in the metallic material.

2. The inclusion rating method according to claim 1, wherein the amount of the hydrogen in the test specimen is 0.3 wppm or more.

3. The inclusion rating method according to claim 2, wherein the amount of the hydrogen in the test specimen is 0.6 wppm or more.

4. The inclusion rating method according to claim 1, wherein a hardness of the test specimen is HV 400 or more.

5. The inclusion rating method according to claim 4, wherein the hardness of the test specimen is HV 450 or more.

6. The inclusion rating method according to claim 5, wherein the hardness of the test specimen is HV 500 or more.

7. An inclusion rating method using a tensile test, the method comprising:
   actively charging a test specimen made of metallic material with hydrogen such that an amount of hydrogen in the test specimen is 0.2 wppm or more;
   carrying out the tensile test on the test specimen to cause a fracture originating from a nonmetallic inclusion affected by hydrogen in the test specimen;
   identifying a type of the nonmetallic inclusion;
   measuring a projected area of the nonmetallic inclusion projected in a direction of a tensile axis of the tensile test, and
   estimating the size of the largest nonmetallic inclusion in the metallic material by analyzing a square root of the projected area using an extreme value statistics
   wherein a hardness of the test specimen is HV 400 or more.

8. The inclusion rating method according to claim 7, wherein the amount of the hydrogen in the test specimen is 0.3 wppm or more.

9. The inclusion rating method according to claim 8, wherein the amount of the hydrogen in the test specimen is 0.6 wppm or more.

10. The inclusion rating method according to claim 7, wherein the hardness of the test specimen is HV 450 or more.

11. The inclusion rating method according to claim 10, wherein the hardness of the test specimen is HV 500 or more.

12. The inclusion rating method according to claim 1, wherein the step of actively charging the test specimen with hydrogen comprises:
   actively charging the metallic material with hydrogen; and
   fabricating the test specimen from the metallic material charged with hydrogen.

13. The inclusion rating method according to claim 1, wherein the test specimen is actively charged with hydrogen before or during the tensile test.

14. The inclusion rating method according to claim 7, wherein the step of actively charging the test specimen with hydrogen comprises:
   actively charging the metallic material with hydrogen; and
   fabricating the test specimen from the metallic material charged with hydrogen.

15. The inclusion rating method according to claim 7, wherein the test specimen is actively charged with hydrogen before or during the tensile test.

* * * * *